US012502461B2

(12) United States Patent
Shi

(10) Patent No.: US 12,502,461 B2
(45) Date of Patent: Dec. 23, 2025

(54) COATING WITH STRONG ADHESION FOR MEDICAL MAGNESIUM ALLOYS AND PREPARATION THEREOF

(71) Applicant: SUZHOU INNOTECH MEDICAL TECHNOLOGY CO., LTD., Suzhou (CN)

(72) Inventor: Chen Shi, Suzhou (CN)

(73) Assignee: SUZHOU INNOTECH MEDICAL TECHNOLOGY CO., LTD., Jiangsu (CN)

( * ) Notice: Subject to any disclaimer, the term of this patent is extended or adjusted under 35 U.S.C. 154(b) by 0 days.

(21) Appl. No.: 18/175,628

(22) Filed: Feb. 28, 2023

(65) Prior Publication Data

US 2023/0201429 A1 Jun. 29, 2023

Related U.S. Application Data

(63) Continuation of application No. PCT/CN2022/115084, filed on Aug. 26, 2022.

(30) Foreign Application Priority Data

Feb. 16, 2022 (CN) ......................... 202210143553.7

(51) Int. Cl.
*C23C 22/60* (2006.01)
*A61L 27/32* (2006.01)
(Continued)

(52) U.S. Cl.
CPC ........... *A61L 31/086* (2013.01); *A61L 31/022* (2013.01); *A61L 31/10* (2013.01); *A61L 31/16* (2013.01);
(Continued)

(58) Field of Classification Search
CPC ...... A61L 31/022; A61L 31/086; A61L 31/10; A61L 31/16; B05D 2202/20;
(Continued)

(56) References Cited

U.S. PATENT DOCUMENTS

2010/0191324 A1 7/2010 Klocke
2020/0109474 A1* 4/2020 Ueda ....................... C22C 23/00

FOREIGN PATENT DOCUMENTS

CN 101411892 A 4/2009
CN 101461964 A 6/2009
(Continued)

*Primary Examiner* — Lois L Zheng

(57) ABSTRACT

A coating with strong adhesion for medical magnesium alloys, including a magnesium phosphate or calcium phosphate layer as an inner layer and a hydrophobic polymer layer as an outer layer. The inner layer is attached to the medical magnesium alloy; and the outer layer is attached to the inner layer. A preparation method of the coating is also provided, including: (S1) carrying out surface treatment on a medical magnesium alloy substrate; (S2) preparing a solution including magnesium salt/calcium salt and phosphoric acid/phosphate followed by pH adjustment and heating; (S3) soaking the medical magnesium alloy substrate in the solution followed by washing and drying to obtain a magnesium phosphate/calcium phosphate layer-coated medical magnesium alloy sample; and (S4) depositing a hydrophobic polymer layer on the medical magnesium alloy sample through chemical vapor deposition (CVD).

9 Claims, 2 Drawing Sheets

(51) Int. Cl.

| | |
|---|---|
| ***A61L 31/02*** | (2006.01) |
| ***A61L 31/08*** | (2006.01) |
| ***A61L 31/10*** | (2006.01) |
| ***A61L 31/16*** | (2006.01) |
| ***B05D 1/00*** | (2006.01) |
| ***B05D 3/10*** | (2006.01) |
| ***C23C 22/22*** | (2006.01) |

(52) U.S. Cl.

CPC ............... *B05D 1/62* (2013.01); *B05D 3/102* (2013.01); *C23C 22/22* (2013.01); *A61L 2420/02* (2013.01); *A61L 2420/08* (2013.01); *A61L 2430/02* (2013.01)

(58) Field of Classification Search

CPC B05D 2350/10; B05D 2350/60; C23C 22/57; C23C 22/60

See application file for complete search history.

(56) References Cited

FOREIGN PATENT DOCUMENTS

| | | | | | |
|---|---|---|---|---|---|
| CN | 103451640 | A | | 12/2013 | |
| CN | 103933611 | A | | 7/2014 | |
| CN | 107281543 | A | * | 10/2017 | ............ C23C 22/34 |
| CN | 109692360 | A | | 4/2019 | |
| CN | 114533955 | A | | 5/2022 | |
| DE | 102008040640 | A1 | | 1/2010 | |
| KR | 101357673 | B1 | | 2/2014 | |
| WO | WO2020196777 | | * | 10/2020 | ................ C25F 3/18 |

* cited by examiner

COATING WITH STRONG ADHESION FOR MEDICAL MAGNESIUM ALLOYS AND PREPARATION THEREOF

CROSS-REFERENCE TO RELATED APPLICATIONS

This application is a continuation of International Patent Application No. PCT/CN2022/115084, filed on Aug. 26, 2022, which claims the benefit of priority from Chinese Patent Application No. 202210143553.7, filed on Feb. 16, 2022. The content of the aforementioned application, including any intervening amendments thereto, is incorporated herein by reference in its entirety.

TECHNICAL FIELD

This application relates to biomedical metallic materials, and more particularity to a coating with strong adhesion for medical magnesium alloys and a preparation thereof.

BACKGROUND

In view of similar density, elastic modulus and yield strength to natural bone, the medical magnesium alloy can effectively avoid the "stress shielding" effect, thus being considered as ideal fixation materials for bone implants. Compared with other orthopedic implants, such as stainless steel, titanium alloy and cobalt-chromium alloy, the medical magnesium alloy has good biodegradability, and will undergo self-degradation after being implanted, so that it does not need to be removed by another operation, greatly relieving the pain of patients. Unfortunately, the medical magnesium alloy is chemically active, and has a large degradation rate in vivo, which will easily cause the accumulation of degradation products such as magnesium ions and hydrogen, causing harm to the human health.

In order to retard the degradation of the medical magnesium alloy in vivo, it is usually to apply a polymer hydrophobic coating such as polylactic acid on the medical magnesium alloy to prevent the medical magnesium alloy from being directly exposed to other substances, such as body fluids and blood (these substances in vivo need to penetrate through the coating to undergo contact reaction with the medical magnesium alloy).

Nevertheless, the adhesion of the polymer hydrophobic coating (e.g., polylactic acid) to the medical magnesium alloy substrate is insufficient, such that the coating is prone to falling off the substrate during use. The area without coated will be exposed to other in-vivo substances and undergo rapid degradation, which will further lead to rapid degradation in other parts. As a consequence, the excess accumulation of degradation products in vivo will still occur, and cause harm to the human body.

SUMMARY

An object of this application is to provide a coating with strong adhesion for medical magnesium alloys and a preparation thereof to overcome the problem that the existing coating is prone to falling off the medical magnesium alloy substrate due to the insufficient adhesion strength.

Technical solutions of the disclosure are described as follows.

In a first aspect, this application provides a coating for a medical magnesium alloy, comprising:

an inner layer; and an outer layer;

wherein the inner layer is a magnesium phosphate layer or a calcium phosphate layer, and is configured to adhere to a surface of the medical magnesium alloy; and the outer layer is a hydrophobic polymer layer, and adheres to a surface of the inner layer.

In a second aspect, this application provides a method for preparing the above coating, comprising:

(S1) subjecting a medical magnesium alloy substrate to surface treatment;

(S2) preparing a solution containing a magnesium salt or calcium salt and phosphoric acid or a phosphate followed by pH adjustment and heating to 5-99° C.;

(S3) soaking the medical magnesium alloy substrate in the solution for 5 min-12 h, followed by washing and drying to obtain a magnesium phosphate or calcium phosphate layer-coated medical magnesium alloy sample; and (S4) depositing a hydrophobic polymer layer on a surface of the magnesium phosphate or calcium phosphate layer-coated medical magnesium alloy sample through chemical vapor deposition (CVD).

In some embodiments, in step (S2), the phosphate is selected from the group consisting of sodium phosphate, potassium phosphate, magnesium phosphate, ammonium phosphate, calcium phosphate and a combination thereof.

In some embodiments, in step (S2), the magnesium salt is selected from the group consisting of magnesium chloride, magnesium sulfate, magnesium nitrate, magnesium hydroxide, magnesium phosphate, magnesium carbonate, magnesium perchlorate, magnesium citrate, ethylenediaminetetraacetic acid (EDTA) disodium magnesium salt (EDTA-Mg), magnesium bromide, magnesium iodide and a combination thereof.

In some embodiments, in step (S2), the calcium salt is selected from the group consisting of calcium phosphate, EDTA calcium disodium salt (EDTA-Ca), calcium citrate, calcium acetate, calcium chloride, calcium nitrate, calcium maleate, calcium polyacrylate, calcium polymethacrylate and a combination thereof.

In some embodiments, in step (S2), a molar concentration ratio of magnesium ion or calcium ion to phosphate ion in the solution is (0.5-2):1.

In some embodiments, in step (S2), the molar concentration ratio of magnesium ion or calcium ion to phosphate ion in the solution is (0.8-1.2):1.

In some embodiments, in step (S2), the pH adjustment is performed by adjusting the solution to pH 2-10 with nitric acid, sulfuric acid, hydrochloric acid, phosphoric acid, acetic acid, sodium hydroxide, calcium hydroxide, potassium hydroxide, magnesium hydroxide, aqueous ammonia or a combination thereof.

In some embodiments, in step (S4), the hydrophobic polymer layer is made of Parylene, polymethyl methacrylate (PMMA), Polystyrene (PS), polyurethane or a silicone resin.

In some embodiments, the method further comprises:

applying a drug-loading coating on a surface of the hydrophobic polymer layer;

wherein the drug-loading coating is made of polylactic acid, polyglycolide, polycaprolactone or polyurethane.

Compared to the prior art, this application has the following beneficial effects.

Regarding the coating provided herein, a magnesium phosphate or calcium phosphate layer is arranged between the medical magnesium alloy substrate and the hydrophobic polymer layer to enable the strong adhesion therebetween. The magnesium phosphate or calcium phosphate layer not only has strong adhesion to the surface of the medical magnesium alloy substrate, but also provides an adhesion site for the hydrophobic polymer layer, contributing to the adhesion of the hydrophobic polymer layer to the surface of the magnesium phosphate or calcium phosphate layer. The coating provided herein has enhanced adhesion to the medical magnesium alloy substrate, and thus is not easy to fall off. According to test results, the bonding strength between the coating and the medical magnesium alloy substrate can reach more than 40 MPa at a physiological temperature.

BRIEF DESCRIPTION OF THE DRAWINGS

The accompany drawings needed in the description of the embodiments of the disclosure or the prior art will be briefly described below to explain the technical solutions of the present disclosure or the prior art more clearly. Obviously, presented in the accompany drawings are merely some embodiments of the present disclosure, and other drawings can be obtained by those skilled in the art based on the drawings provided herein without paying creative effort.

DETAILED DESCRIPTION OF EMBODIMENTS

Figure 1:
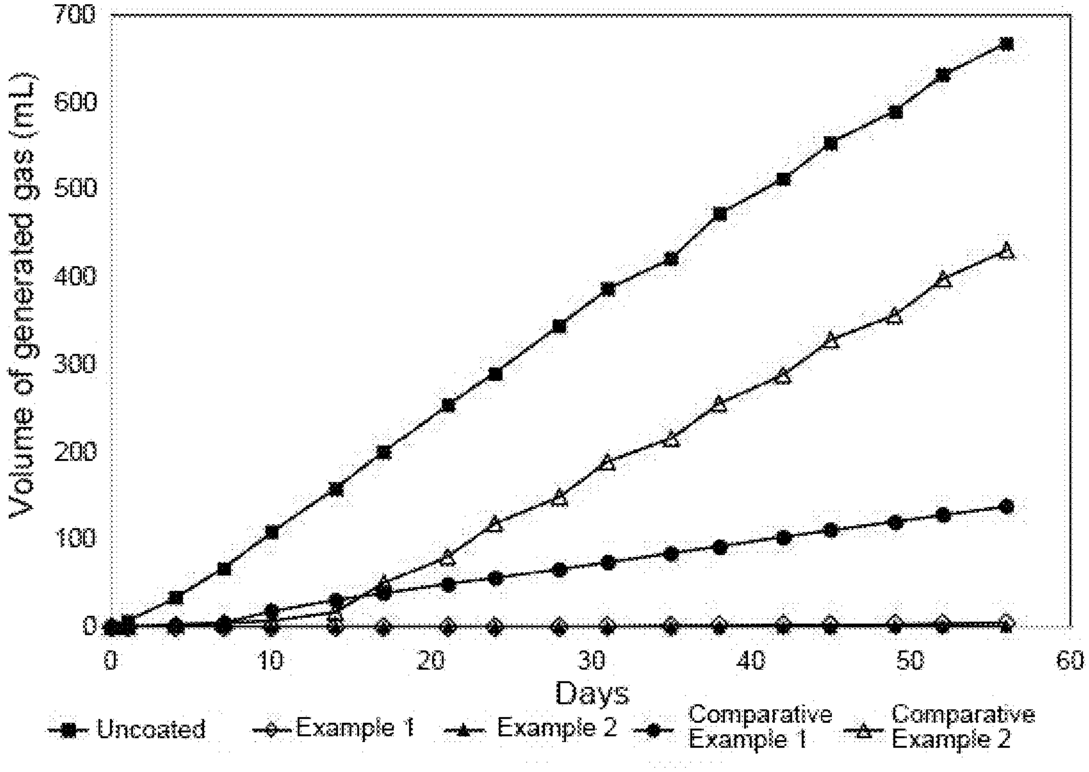
FIG. 1 shows gas generation curves in the case of soaking magnesium alloy samples in normal saline.

The disclosure will be described completely and clearly below with reference to the accompanying drawings and embodiments to make the object, technical solutions, and beneficial effects of the present disclosure clearer. Obviously, provided below are merely some embodiments of the disclosure, which are not intended to limit the disclosure. Based on the embodiments of the present disclosure, all other embodiments obtained by those skilled in the art without paying any creative effort shall fall within the scope of the present disclosure.

This application provides a coating with strong adhesion for medical magnesium alloys and a preparation thereof to overcome the problem that the adhesion of the hydrophobic polymer layer to the medical magnesium alloy substrate is insufficient, effectively preventing the coating from peeling off the substrate.

In an embodiment, the medical magnesium alloy is ZK60 magnesium alloy.

In an embodiment, the phosphate is selected from the group consisting of sodium phosphate, potassium phosphate, magnesium phosphate, ammonium phosphate, calcium phosphate and a combination thereof.

In an embodiment, the magnesium salt is selected from the group consisting of magnesium chloride, magnesium sulfate, magnesium nitrate, magnesium hydroxide, magnesium phosphate, magnesium carbonate, magnesium perchlorate, magnesium citrate, EDTA-Mg, magnesium bromide, magnesium iodide and a combination thereof.

In an embodiment, the calcium salt is selected from the group consisting of calcium phosphate, EDTA-Ca, calcium citrate, calcium acetate, calcium chloride, calcium nitrate, calcium maleate, calcium polyacrylate, calcium polymethacrylate and a combination thereof.

In an embodiment, the pH is adjusted with nitric acid, sulfuric acid, hydrochloric acid, phosphoric acid, acetic acid, sodium hydroxide, calcium hydroxide, potassium hydroxide, magnesium hydroxide, aqueous ammonia or a combination thereof.

Since there are a variety of options for individual materials, they are not enumerated in the embodiments of the present application.

Example 1

Provided herein was a coating with strong adhesion for medical magnesium alloys, including an inner layer and an outer layer. The inner layer was a magnesium phosphate layer, and adhered to a surface of a medical magnesium alloy substrate. The outer layer was a Parylene layer, and adhered to a surface of the inner layer.

The coating was prepared through the following steps.

(S1) The ZK60 magnesium alloy was machined to a desired shape, and subjected to ultrasonic cleaning in anhydrous acetone for 5 min to remove surface oil, washing and blow drying.

(S2) A solution containing magnesium nitrate and sodium dihydrogen phosphate was prepared, adjusted to pH 3.5 with dilute nitric acid, and heated to 75° C. under a water bath, where a molar concentration ratio of magnesium ions to phosphate ions in the solution was 1:1.

(S3) The ZK60 magnesium alloy was soaked in the solution for 60 min, washed with deionized water and dried to obtain a magnesium phosphate layer-coated ZK60 magnesium alloy sample.

(S4) A Parylene layer was deposited on a surface of the magnesium phosphate layer-coated ZK60 magnesium alloy sample through CVD to obtain the desired coating, where a thickness of the Parylene layer was 15 μm.

Example 2

Provided herein was a coating with strong adhesion for medical magnesium alloys, including an inner layer and an outer layer. The inner layer was a calcium phosphate layer, and adhered to a surface of the medical magnesium alloy substrate. The outer layer was a Parylene layer, and adhered to a surface of the inner layer.

The coating was prepared through the following steps.

(S1) The ZK60 magnesium alloy was machined to a desired shape, and subjected to ultrasonic cleaning in anhydrous acetone for 5 min to remove surface oil, washing and blow drying.

(S2) A solution containing EDTA-Ca and potassium dihydrogen phosphate was prepared, adjusted to pH 8.0 with potassium hydroxide, and heated to 90° C., where a molar concentration ratio of calcium ions to phosphate ions in the solution was 1:1.

(S3) The ZK60 magnesium alloy was soaked in the solution for 180 min, washed with deionized water and dried to obtain a calcium phosphate layer-coated ZK60 magnesium alloy sample.

(S4) A Parylene layer was deposited on a surface of the calcium phosphate layer-coated ZK60 magnesium alloy sample through CVD to obtain the desired coating, where a thickness of the Parylene layer was 45 μm.

Example 3

Provided herein was a coating with strong adhesion for medical magnesium alloys, including an inner layer and an outer layer. The inner layer was a calcium phosphate layer, and adhered to a surface of the medical magnesium alloy substrate. The outer layer was a Parylene layer, and adhered to a surface of the inner layer.

The coating was prepared through the following steps.

(S1) The ZK60 magnesium alloy was machined to a desired shape, and subjected to ultrasonic cleaning in anhydrous acetone for 5 min to remove surface oil, washing and blow drying.

(S2) A solution containing EDTA-Ca and potassium dihydrogen phosphate was prepared, adjusted to pH 8.5 with potassium hydroxide, and heated to 90° C., where a molar concentration ratio of calcium ions to phosphate ions in the solution was 0.5:1.

(S3) The ZK60 magnesium alloy was soaked in the solution for 180 min, washed with deionized water and dried to obtain a calcium phosphate layer-coated ZK60 magnesium alloy sample.

(S4) A Parylene layer was deposited on a surface of the calcium phosphate layer-coated ZK60 magnesium alloy sample through CVD to obtain the desired coating, where a thickness of the Parylene layer was 28 μm.

Example 4

Provided herein was a coating with strong adhesion for medical magnesium alloys, including an inner layer and an outer layer. The inner layer was a calcium phosphate layer, and adhered to a surface of the medical magnesium alloy substrate. The outer layer was a Parylene layer, and adhered to a surface of the inner layer.

The coating was prepared through the following steps.

(S1) The ZK60 magnesium alloy was machined to a desired shape, and subjected to ultrasonic cleaning in anhydrous acetone for 5 min to remove surface oil, washing and blow drying.

(S2) A solution containing EDTA-Ca and sodium dihydrogen phosphate was prepared, adjusted to pH 8.0 with sodium hydroxide, and heated to 90° C., where a molar concentration ratio of calcium to phosphate ions in the solution was 0.8:1.

(S3) The ZK60 magnesium alloy was soaked in the solution for 180 min, washed with deionized water and dried to obtain a calcium phosphate layer-coated ZK60 magnesium alloy sample.

(S4) A Parylene layer was deposited on a surface of the calcium phosphate layer-coated ZK60 magnesium alloy sample through CVD to obtain the desired coating, where a thickness of the Parylene layer was 35 μm.

Example 5

Provided herein was a coating with strong adhesion for medical magnesium alloys, including an inner layer and an outer layer. The inner layer was a calcium phosphate layer, and adhered to a surface of the medical magnesium alloy substrate. The outer layer was a Parylene layer, and adhered to a surface of the inner layer.

The coating was prepared through the following steps.

(S1) The ZK60 magnesium alloy was machined to a desired shape, and subjected to ultrasonic cleaning in anhydrous acetone for 5 min to remove surface oil, washing and blow drying.

(S2) A solution containing EDTA-Ca and potassium dihydrogen phosphate was prepared, adjusted to pH 8.0 with potassium hydroxide, and heated to 90° C., where a molar concentration ratio of calcium ions to phosphate ions in the solution was 1.2:1.

(S3) The ZK60 magnesium alloy was soaked in the solution for 180 min, washed with deionized water and dried to obtain a calcium phosphate layer-coated ZK60 magnesium alloy sample.

(S4) A Parylene layer was deposited on a surface of the calcium phosphate layer-coated ZK60 magnesium alloy sample through CVD to obtain the desired coating, where a thickness of the Parylene layer was 45 μm.

Example 6

Provided herein was a coating with strong adhesion for medical magnesium alloys, including an inner layer and an outer layer. The inner layer was a calcium phosphate layer, and adhered to a surface of the medical magnesium alloy substrate. The outer layer was a Parylene layer, and adhered to a surface of the inner layer.

The coating was prepared through the following steps.

(S1) The ZK60 magnesium alloy was machined to a desired shape, and subjected to ultrasonic cleaning in anhydrous acetone for 5 min to remove surface oil, washing and blow drying.

(S2) A solution containing EDTA-Ca and potassium dihydrogen phosphate was prepared, adjusted to pH 8.0 with potassium hydroxide, and heated to 90° C., where a molar concentration ratio of calcium ions to phosphate ions in the solution was 2:1.

(S3) The ZK60 magnesium alloy was soaked in the solution for 180 min, washed with deionized water and dried to obtain a calcium phosphate layer-coated ZK60 magnesium alloy sample.

(S4) A Parylene layer was deposited on a surface of the calcium phosphate layer-coated ZK60 magnesium alloy sample through CVD to obtain the desired coating, where a thickness of the Parylene layer was 45 μm.

Example 7

Provided herein was a coating with strong adhesion for medical magnesium alloys, including an inner layer and an outer layer. The inner layer was a calcium phosphate layer, and adhered to a surface of the medical magnesium alloy substrate. The outer layer was a Parylene layer, and adhered to a surface of the inner layer.

The coating was prepared through the following steps.

(S1) The ZK60 magnesium alloy was machined to a desired shape, and subjected to ultrasonic cleaning in anhydrous acetone for 5 min to remove surface oil, washing and blow drying.

(S2) A solution containing EDTA-Ca and potassium dihydrogen phosphate was prepared, adjusted to pH 8.0 with potassium hydroxide, and heated to 90° C., where a molar concentration ratio of calcium ions to phosphate ions in the solution was 2:1.

(S3) The ZK60 magnesium alloy was soaked in the solution for 180 min, washed with deionized water and dried to obtain a calcium phosphate layer-coated ZK60 magnesium alloy sample.

(S4) A Parylene layer was deposited on a surface of the calcium phosphate layer-coated ZK60 magnesium alloy sample through CVD to obtain the desired coating, where a thickness of the Parylene layer was 45 μm.

(S5) A polyglycolide coating was applied on a surface of the Parylene layer.

Comparative Example 1

Provided herein was a coating with strong adhesion for medical magnesium alloys, which only included a calcium phosphate layer.

The calcium phosphate layer was prepared through the following steps.

(S1) The ZK60 magnesium alloy was machined to a desired shape, and subjected to ultrasonic cleaning in anhydrous acetone for 5 min to remove surface oil, washing and blow drying.

(S2) A solution containing EDTA-Ca and potassium dihydrogen phosphate was prepared, adjusted to pH 8.0 with potassium hydroxide, and heated to 90° C., where a molar concentration ratio of calcium ions to phosphate ions in the solution was 1:1.

(S3) The ZK60 magnesium alloy was soaked in the solution for 180 min, washed with deionized water and dried to obtain a calcium phosphate layer-coated ZK60 magnesium alloy sample.

Comparative Example 2

Provided here is a coating on medical magnesium alloy with a strong binding force, which includes a Parylene layer. The coating was prepared through the following steps.

(S1) The ZK60 magnesium alloy was machined to a desired shape, and subjected to ultrasonic cleaning in anhydrous acetone for 5 min to remove surface oil, washing and blow drying.

(S2) A Parylene layer was deposited on a surface of the ZK60 magnesium alloy through CVD, in which a thickness of the Parylene layer was 45 μm.

Comparative Example 3

AZ31 magnesium alloy was machined to a desired shape, and subjected to ultrasonic cleaning in anhydrous acetone for 5 min to remove surface oil, washing and blow drying, without any surface modifications.

Performance Test

1. Adhesion Strength Test

A universal mechanical testing machine was used to test the adhesion strength between the coatings fabricated in Examples 1 and 2 and the medical magnesium alloy substrate.

The results showed that the adhesion strength between the coating in Example land the medical magnesium alloy substrate was 43 MPa, the adhesion strength between the coating in Example 2 and the medical magnesium alloy substrate was 64 MPa.

2. Gas Generation Test

The magnesium alloy samples prepared in Examples 1-2 and Comparative Examples 1-3 were soaked into normal saline at 37° C. to observe the gas generation, where the normal saline was replaced every 3-4 days. The volume of the gas generated from the degradation of the samples was measured by using a gas measuring cylinder, based on which the gas generation curves were plotted (as shown in FIG. 1).

3. Degradation Property Test

The ZK60 magnesium alloy sample in Example 1 and the AZ31 magnesium alloy sample in Comparative Example 3 were machined into a screw shape. The sample in Example 1 was implanted into the condyle of a goat's left leg; and the sample in Comparative Example 3 was implanted into the condyle of the goat's right leg. The degradation of magnesium alloy screws was observed by CT scanning respectively after 3, 6, 12 and 24 months of the implantation. Results were shown in FIG. 2.

Data Analysis

According to the adhesion strength test, the adhesion strength between the medical magnesium alloy substrate and the coating consisting of a magnesium phosphate or calcium phosphate inner layer and a hydrophobic polymer outer layer (such as Parylene layer) was more than 40 MPa. Particularly, the coating prepared in an alkaline environment had a stronger adhesion to the substrate compared to that prepared in an acidic environment.

Referring to FIG. 1, the gas volume generated from the degradation of the sample in Comparative Example 3 approximately exhibited a linear increase throughout the test process, indicating the rapid degradation of the uncoated medical magnesium alloy in normal saline.

Regarding the samples fabricated in Examples 1-2, almost no gas generation was observed during the nearly 60-day soaking process, indicating that almost no degradation occurred, and the coating consisting of the inner layer and the outer layer can effectively protect the medical magnesium alloy in nearly 60 days.

Regarding the sample fabricated in Comparative Example 1, on the surface of the magnesium alloy substrate there was only coated the magnesium phosphate layer. However, the magnesium phosphate layer had limited effect on preventing the degradation of the medical magnesium alloy in contact with body fluid, therefore, the medical magnesium alloy was gradually degraded and the gas was gradually produced with soaking.

Regarding Comparative Example 2, there was only the Parylene layer coated on the surface of the medical magnesium alloy substrate. No generation was observed during 7 days soaking process since the Parylene layer had good hydrophobicity and provided protection for the sample at the initial stage of degradation. Whereas, as the surface of the medical magnesium alloy substrate lacked attachment sites with the Parylene layer, the adhesion between the Parylene layer and the medical magnesium alloy substrate was weak, the Parylene layer was thus gradually peeled off and damaged in the soaking process, therefore, the medical magnesium alloy substrate contacted with the solution and was quickly degraded, thereby generating a large number of bubbles. As a result, the gas volume generated from the degradation increased after 7 days of soaking.

Accordingly, the calcium phosphate layer provided a large number of attachment sites for the Parylene layer, and the Parylene layer was tightly attached to the surface of the calcium phosphate layer, leading to a significant improvement of adhesion between the coating and the medical magnesium alloy substrate. In addition, the inner layer and the outer layer contributed to slower degradation speed and longer degradation time of the medical magnesium alloy substrate.

Figure 2:
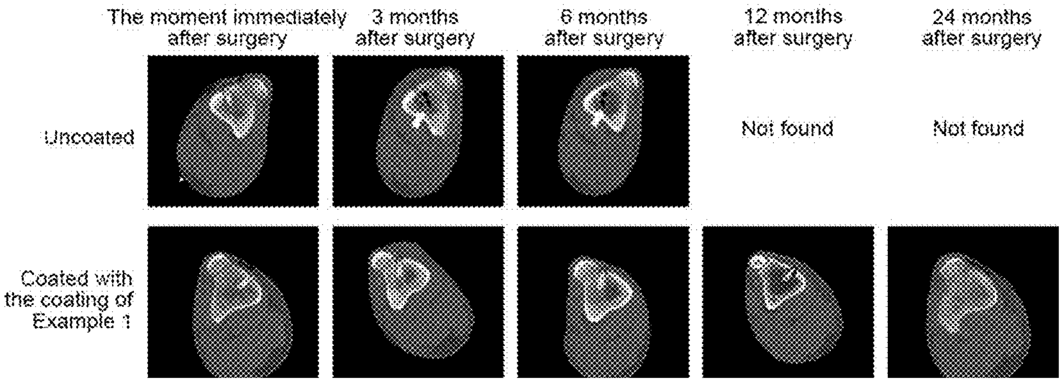
FIG. 2 shows computed tomography (CT) scanning images illustrating degradation of a magnesium alloy screw over time after implanted in a goat.

Referring to FIG. 2, the uncoated medical magnesium alloy screw began to degrade and generate a large amount of gas upon implanted into the goat, leading to cavities in bone tissue (where the arrow points in FIG. 2). After 6 months implantation, the uncoated medical magnesium alloy screw was almost completely degraded. After 12 months and 24 months implantation, no medical magnesium alloy screw was observed. On the contrary, the medical magnesium alloy screw with double layers provided herein was evident within 12 months, and a thread structure thereof almost remained unchanged. After 24 months, the medical magnesium alloy screw with double layers almost disappeared.

Accordingly, the medical magnesium alloy screw with the magnesium phosphate layer or the calcium phosphate layer as the inner layer and the hydrophobic polymer layer as the outer layer degraded slowly within 12 months, and degraded completely within 12-24 months.

Compared to the prior art, this application has the following beneficial effects.

(1) Regarding the coating provided herein, a magnesium phosphate or calcium phosphate layer is arranged between the medical magnesium alloy substrate and the hydrophobic polymer layer to enable the strong adhesion therebetween. The magnesium phosphate or calcium phosphate layer not only has strong adhesion to the surface of the medical magnesium alloy substrate, but also provides an adhesion site for the hydrophobic polymer layer, contributing to the adhesion of the hydrophobic polymer layer to the surface of the magnesium phosphate or calcium phosphate layer. The coating provided herein has enhanced adhesion to the medical magnesium alloy substrate, and thus is not easy to fall off. According to test results, the bonding strength between the coating and the medical magnesium alloy substrate can reach more than 40 MPa at a physiological temperature.

(2) The medical magnesium alloy provided herein can be protected by the inner layer and the outer layer, thus almost no degradation within 60 days was observed. The inner layer and the outer layer contribute to slower degradation speed and longer degradation time of the medical magnesium alloy.

(3) The medical magnesium alloy provided herein can maintain the structural integrity for 6-12 months after implantation, facilitating promoting the healing and growth of surrounding tissues. The degradation of medical magnesium alloy implants occurs after 12-24 months of the implantation.

Described above are merely illustrative of the disclosure, and are not intended to limit the disclosure. Although the disclosure has been illustrated and described in detail above, it should be understood that those skilled in the art could still make modifications and replacements to the embodiments of the disclosure. Those modifications and replacements made by those skilled in the art without departing from the scope of the disclosure shall fall within the scope of the present disclosure defined by the appended claims.

What is claimed is:

1. A method for preparing a coating for medical magnesium alloys, comprising:

(S1) machining a medical magnesium alloy substrate into a screw shape, and subjecting the medical magnesium alloy substrate to surface treatment;

(S2) preparing a solution containing a magnesium salt or calcium salt and a phosphate followed by pH adjustment to pH 8-10 and heating to 5-99° C.;

(S3) soaking the medical magnesium alloy substrate in the solution for 5 min-12 h, followed by washing and drying to obtain a magnesium phosphate or calcium phosphate layer-coated medical magnesium alloy sample; and (S4) depositing a hydrophobic polymer layer on a surface of the magnesium phosphate or calcium phosphate layer-coated medical magnesium alloy sample through chemical vapor deposition (CVD).

2. The method of claim 1, wherein in step (S2), the phosphate is selected from the group consisting of sodium phosphate, potassium phosphate, magnesium phosphate, ammonium phosphate, calcium phosphate and a combination thereof.

3. The method of claim 1, wherein in step (S2), the magnesium salt is selected from the group consisting of magnesium chloride, magnesium sulfate, magnesium nitrate, magnesium hydroxide, magnesium phosphate, magnesium carbonate, magnesium perchlorate, magnesium citrate, ethylenediaminetetraacetic acid (EDTA) disodium magnesium salt (EDTA-Mg), magnesium bromide, magnesium iodide and a combination thereof.

4. The method of claim 1, wherein in step (S2), the calcium salt is selected from the group consisting of calcium phosphate, EDTA calcium disodium salt (EDTA-Ca), calcium citrate, calcium acetate, calcium chloride, calcium nitrate, calcium maleate, calcium polyacrylate, calcium polymethacrylate and a combination thereof.

5. The method of claim 1, wherein in step (S2), a molar concentration ratio of magnesium ion or calcium ion to phosphate ion in the solution is (0.5-2):1.

6. The method of claim 5, wherein in step (S2), the molar concentration ratio of magnesium ion or calcium ion to phosphate ion in the solution is (0.8-1.2):1.

7. The method of claim 1, wherein in step (S2), the pH adjustment is performed by adjusting the solution with sodium hydroxide, calcium hydroxide, potassium hydroxide, magnesium hydroxide, aqueous ammonia or a combination thereof.

8. The method of claim 1, wherein in step (S4), the hydrophobic polymer layer is made of Parylene, polyurethane, polymethyl methacrylate (PMMA), Polystyrene (PS) or a silicone resin.

9. The method of claim 1, further comprising:

applying a drug-loading coating on a surface of the hydrophobic polymer layer;

wherein the drug-loading coating is made of polylactic acid, polyglycolide, polycaprolactone or polyurethane.

* * * * *